(12) United States Patent
Leguijt et al.

(10) Patent No.: US 9,272,981 B1
(45) Date of Patent: Mar. 1, 2016

(54) METHOD OF PREPARING A COMPOUND

(71) Applicant: Amazon Technologies, Inc., Seattle, WA (US)

(72) Inventors: Robin Leguijt, Eindhoven (NL); Marcel Van Der Sluis, Eelderwolde (NL)

(73) Assignee: Amazon Technologies, Inc., Seattle, WA (US)

( * ) Notice: Subject to any disclaimer, the term of this patent is extended or adjusted under 35 U.S.C. 154(b) by 0 days.

(21) Appl. No.: 14/747,648

(22) Filed: Jun. 23, 2015

(51) Int. Cl.
  *C07C 50/34* (2006.01)
  *C09B 1/28* (2006.01)
  *C09B 1/515* (2006.01)
  *C07C 46/00* (2006.01)
  *C07C 225/36* (2006.01)

(52) U.S. Cl.
  CPC ............... *C07C 225/36* (2013.01); *C07C 50/34* (2013.01)

(58) Field of Classification Search
  CPC ............ C09B 1/515; C09B 1/28; C07C 46/00
  See application file for complete search history.

(56) References Cited

FOREIGN PATENT DOCUMENTS

| FR | 1331168 | * | 5/1963 |
| GB | WO2010/031860 A2 | * | 3/2010 |
| WO | 2010031860 A2 | | 3/2010 |

OTHER PUBLICATIONS

Zaragoza Dorwald, Side Reactions in Organic Synthesis, 2005, Wiley-VCH Verlag GmbH & Co. KGaA, Weinheim, Preface. p. IX.*

* cited by examiner

*Primary Examiner* — Paul A Zucker
(74) *Attorney, Agent, or Firm* — EIP US LLP

(57) ABSTRACT

A method of preparing a compound corresponding to general formula (3):

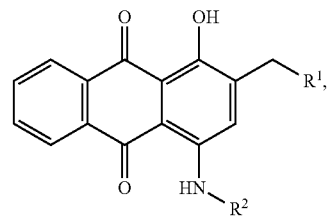

(3)

$R^1$ and $R^2$ each independently being an alkyl group, and the method comprising reacting a compound corresponding to general formula (2):

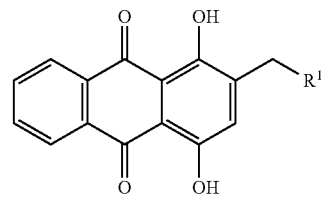

(2)

with an alkylamine corresponding to general formula (4):
$H_2N-R^2$ (4).

25 Claims, 2 Drawing Sheets

R[1] = an alkyl group
R[2] = an alkyl group

METHOD OF PREPARING A COMPOUND

BACKGROUND

It is common for a compound to be prepared in a laboratory, on a small scale, when the compound is being tested for suitability for a commercial product. Then, for bulk manufacture of the product, there may be limitations in for example the purity of the product or practicalities in the apparatus or reagents required for preparing the compound using the same method as used in the laboratory.

Hence, it is desirable to devise a method appropriate for preparing the compound on an industrial scale.

DETAILED DESCRIPTION

An electrowetting display device 1 for example includes a plurality of picture elements or display elements, which may also be referred to as an electrowetting cell or an electrowetting pixel. Further details of examples are described later. In such an electrowetting cell, there are for example two fluids which are substantially immiscible with each other. One or both of these fluids may comprise a dye, for modifying a colour characteristic of light passing through the fluid. In this way an electrowetting cell can be used to control a display effect displayed by the electrowetting display device.

In examples, a first fluid of the fluids in such an electrowetting cell may comprise an alkane or silicone oil, for example. A compound represented by general formula (3):

(3)

may be dissolved in the first fluid. Such a compound may act as a dye when dissolved in the first fluid. Such a compound may be 2-(2-ethylhexyl)-4-((2-ethylhexyl)amino)-1-hydroxyanthracene-9,10-dione, if for example $R^1$ has the formula (6) and $R^2$ has the formula (7) described later.

Figure 3:
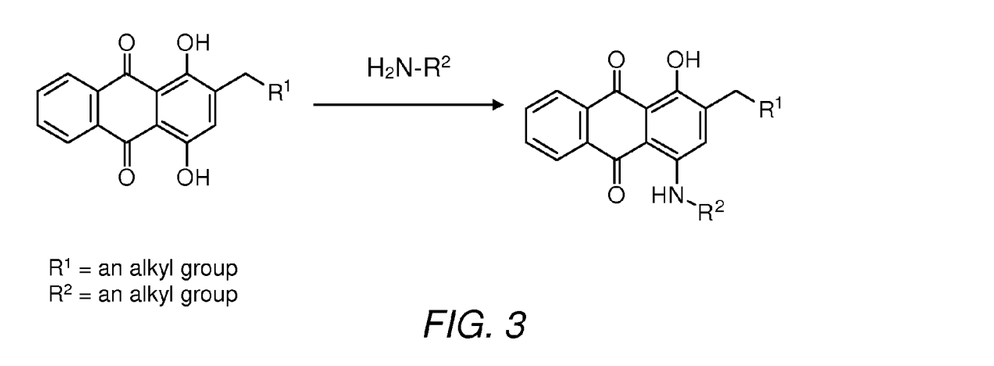
FIG. 3 shows a diagram of a method according to examples.

A new method of preparing the compound represented by general formula (3) will now be described generally, followed then by specific examples. Compared with known methods, the new method is suitable for preparing the compound represented by general formula (3) on an industrial scale, as the compounds represented by general formula (2) (as described later) and (3) prepared during the new method are obtained in a manner which enables crystallisation to be employed for obtaining the prepared compounds represented by general formula (2) and (3) with an acceptable purity and yield for industrial scale manufacture. This may be, for example, due to at least one of, or a combination of any of: a purity of the compounds represented by general formula (2) and (3) prepared; the purity and inherent crystallisable tendency of any intermediate compound formed in the reaction, including for example the compound represented by general formula (2); or the tendency of any by-products of Reactions RI and/or RII described later not to inhibit or poison crystallising of the compounds represented by the general formula (2) and (3). Further details of examples of the method are explained below. Reference to FIG. 3 may also be made in this respect.

In examples, the method of preparing the compound represented by general formula (3) includes reacting a compound represented by general formula (2):

(2)

with an alkylamine represented by general formula (4):

$H_2N-R^2$ (4).

The compound represented by general formula (2) may be referred to as 2-(2-ethylhexyl)-1,4-dihydroxyanthracene-9,10-dione if $R^1$ has the formula (6) described below.

$R^1$ and $R^2$ are each independently an alkyl group which is for example a straight chain or a branched alkyl group.

In examples, the alkyl group $R^1$ has one or more carbon atoms, for example in some examples 1 to 21 carbon atoms, for example 1, 2, 3, 4, 5, 6, 7, 8, 9, 10, 11, 12, 13, 14, 15, 16, 17, 18, 19, 20 or 21 carbon atoms.

In examples, the alkyl group $R^2$ has one or more carbon atoms, for example in some examples 1 to 22 carbon atoms, for example 1, 2, 3, 4, 5, 6, 7, 8, 9, 10, 11, 12, 13, 14, 15, 16, 17, 18, 19, 20, 21 or 22 carbon atoms.

In examples, $R^1$ is a straight chain alkyl group having 1 to 21 carbon atoms, for example 1, 2, 3, 4, 5, 6, 7, 8, 9, 10, 11, 12, 13, 14, 15, 16, 17, 18, 19, 20 or 21 carbon atoms; in other examples, $R^1$ is a branched chain alkyl group having 3 to 21 carbon atoms, for example 3, 4, 5, 6, 7, 8, 9, 10, 11, 12, 13, 14, 15, 16, 17, 18, 19, 20 or 21 carbon atoms.

In examples, $R^2$ is a straight chain alkyl group having 1 to 22 carbon atoms, for example 1, 2, 3, 4, 5, 6, 7, 8, 9, 10, 11, 12, 13, 14, 15, 16, 17, 18, 19, 20, 21 or 22 carbon atoms; in other examples $R^2$ is a branched chain alkyl group having 3 to 22 carbon atoms, for example 3, 4, 5, 6, 7, 8, 9, 10, 11, 12, 13, 14, 15, 16, 17, 18, 19, 20, 21 or 22 carbon atoms.

In further examples, $R^1$ is a straight chain alkyl group having 1 to 7 carbon atoms, for example with 1, 2, 3, 4, 5, 6 or 7 carbon atoms; in other examples, $R^1$ is a branched chain alkyl group having 3 to 7 carbon atoms, for example 3, 4, 5, 6 or 7 carbon atoms.

In other examples, $R^2$ is a straight chain alkyl group having 1 to 8 carbon atoms, for example with 1, 2, 3, 4, 5, 6, 7 or 8 carbon atoms; in other examples, $R^2$ is a branched chain alkyl group having 3 to 8 carbon atoms, for example 3, 4, 5, 6, 7 or 8 carbon atoms.

In further examples $R^1$ is a straight chain alkyl group having 7 carbon atoms; in other examples, $R^1$ is a branched chain alkyl group having 7 carbon atoms.

In further examples $R^2$ is a straight chain alkyl group having 8 carbon atoms; in other examples, $R^2$ is a branched chain alkyl group having 8 carbon atoms.

In further examples, $R^1$ is an alkyl group represented by general formula (6):

(6)

In other examples, $R^2$ is an alkyl group represented by general formula (7):

(7)

Such examples with $R^1$ being an alkyl group with 7 carbon atoms and/or $R^2$ being an alkyl group with 8 carbon atoms assist dissolution of the compound represented by general formula (3) in an alkane or a silicone oil which may for example be commonly used in the first fluid of an electrowetting cell, though it is to be appreciated that alkyl groups with a different number of carbon atoms, in accordance with other examples described herein, may also assist dissolution in the same or a different first fluid.

The alkylamine represented by general formula (4) is a secondary amine, having a nitrogen atom linked to two hydrogen atoms and the alkyl group $R^2$ by respective single bonds.

The reacting the compound represented by general formula (2) with the alkylamine may be represented schematically as follows:

Reaction RII:

The label "Reaction RII" will be used below to concisely refer to the reacting the compound represented by general formula (2) with the alkylamine.

In examples, the reacting the compound represented by general formula (2) with the alkylamine is performed in the presence of at least one of a reducing agent or water ($H_2O$). In other words a reducing agent, water, or a reducing agent and water may be used in the reaction between the compound represented by general formula (2) and the alkylamine. The reducing agent is typically an agent, for example a chemical element such as a metal, or a compound, which may for example donate, in other words transfer, electrons to a reagent to reduce that reagent. The reducing agent may for example be magnesium or zinc, for example zinc dust. The reducing agent may in some examples be solely one reducing agent, or in other examples may be a mixture of more than one reducing agent, for example any of the example reducing agents listed herein. It has been found that using the reducing agent, for example zinc, with in some examples water, may increase the rate of the reaction. An example of zinc which may be used is zinc dust, for example with particle size of less than 10 micrometers being present in greater than or equal to 98% of a sample (available for example from Sigma Aldrich (3050 Spruce St., St. Louis, Mo. 63103, USA) with product no. 209988 and stated particle size of 10 micrometers).

A quantity of the reducing agent used in Reaction RII in examples is less than a stoichiometric amount of the reducing agent. In other words, a molar amount of the reducing agent is less than the molar amount of the compound represented by general formula (2). In other words, a ratio of molar amount of the compound represented by general formula (2) to the molar amount of the reducing agent is 1:<1 or 1:<0.5. In some examples a molar amount of the reducing agent in the range 0.1 to 1 is used. In some examples approximately, for example with acceptable measuring tolerances, a molar amount of 0.5 or 0.35 of the reducing agent may be used.

In examples, Reaction RII is performed without a solvent. In other examples Reaction RII is performed in a solvent, for example a ketone (such as acetone), an alcohol (such as ethanol or methanol), an ether (such as ethyl ether), an ester (such as ethyl acetate), an aromatic hydrocarbon (such as benzene or toluene), a chlorinated solvent (such as dichloromethane or 1,2-dichloroethane) or an amide (such as dimethylformamide or N-methyl-2-pyrrolidone). A solvent is typically a liquid medium, vehicle or carrier, for example, in which a reaction can occur, with at least one of the reagents possibly being dissolved in the solvent. For example, any reactants of the reaction may be added, for example dissolved, in the solvent, so that the reactants can readily react with each other. In examples where Reaction RII is performed without a solvent, it may be considered that the Reaction RII is performed substantially without solvent, for example without solvent other than tolerable amounts of impurities or without any solvent, in other words neat. Thus, the alkylamine reagent is capable of acting as both a reactant and a reaction vehicle. This therefore simplifies the reaction requirements for an industrial scale. For example, the reaction may be less expensive as purchasing of a solvent is not required. Moreover, the reaction may be less hazardous, for example as a potentially flammable solvent may not be required. Also, without a solvent, the process may not need any isolation, recycling, purification or re-use processes for the solvent which might otherwise be needed where a solvent is used. Further, less complicated apparatus may be required for supplying the chemicals required in the reaction. Also, a greater quantity of the product may be produced for a given size of reaction vessel, or a more compact reaction vessel and overall reaction apparatus may be used given the lower volume requirements without a solvent.

In examples, Reaction RII is performed at a temperature in the range of approximately 25 degrees Celsius (° C.) to approximately 75 degrees Celsius, for example 25 to 75 degrees Celsius or 30 to 60 degrees Celsius to within acceptable accuracy of measurement, for example 25 to 75 degrees Celsius or 30 to 60 degrees Celsius. The reaction mixture may be heated stepwise, for example by heating the compound represented by general formula (2) to approximately 30 degrees Celsius, then after adding the reducing agent heating the reaction mixture to approximately 40 to 45 degrees Celsius, then after adding water heating the reaction mixture to approximately 45 to 55 degrees Celsius, then heating the reaction mixture to 60 degrees Celsius. The reaction mixture may then be cooled to room temperature (for example approximately 21 degrees).

In examples, once Reaction RII has progressed sufficiently to be considered complete, for example when sufficient of the product, namely the compound represented by general formula (3), has been produced, an extractive work up may be performed. This work up may be referred to below as W1 and may include partition between water and a solvent that is immiscible with water. The work up may include a neutralisation of the reaction mixture for example with acid such as a carboxylic acid, for example ethanoic acid (otherwise referred to as acetic acid). The carboxylic acid may also react with and therefore remove from the reaction mixture any residual reducing agent such as the zinc dust. Further, in the work up, water (which may be iced) may be added together with a solvent in which the compound represented by general formula (3) dissolves, such that a partition between water and the solvent may be performed for example to remove reactant impurities such as residual compound with general formula (2) from the product mixture of Reaction RH. The solvent in this work up may be an alkane, for example hexane, heptane, pentane, an ether, for example diethyl ether, a chlorinated solvent, for example dichloromethane, trichloromethane, an ester such as ethyl acetate, or an aromatic solvent such as benzene or toluene. An alkane such as hexane or heptane is sufficiently hydrophobic to dissolve hydrophobic compounds such as that with general formula (3). After separation of the aqueous phase and the solvent phase, the aqueous phase including the water may be removed and discarded. Then an alcohol, for example methanol, and water may be added to the product mixture, followed again by separating and discarding the aqueous phase. When the work-up solvent is highly hydrophobic such as an alkane (for example hexane or heptane), the alcohol for example methanol may assist in removing further impurities in the aqueous phase. A further wash with water may be performed, by adding water to the product mixture and then discarding the aqueous phase. After this washing, the product mixture may be concentrated by evaporating solvents from the solvent phase such as the alkane, for example at a temperature of approximately 50 to 70 degrees Celsius, for example 60 degrees Celsius for example at a pressure of less than 35 millibar, for example less than 30 millibar.

In examples, the method further includes, after Reaction RII, crystallising the compound represented by general formula (3) from a solvent with cooling. This crystallising may be referred to below as C2, and the solvent in the crystallising C2 as S3, for clarity when other crystallising and solvents are described later. In some examples where the work up described above is performed, the crystallising C2 is performed after such work up.

The solvent for the crystallising is for example an alcohol, for example a mono-alcohol (i.e. an alcohol with one —OH group), an alcohol containing (i.e. having solely) 2 to 5 carbon atoms, or a mono-alcohol containing 2 to 5 carbon atoms. For example, the solvent is n-butanol, i.e. $CH_3CH_2CH_2CH_2OH$.

Other isomers of such a solvent may be used provided for example they are sufficiently liquid at the crystallisation temperature.

In the crystallising C2 the solvent S3 is for example added to the concentrated product mixture from Reaction RII. At least one cycle of treatment to remove volatile impurities, such as residual solvent used in the work up, with the solvent S3 may be performed, for example by adding the solvent S3 to the concentrated product mixture then evaporating the solvent for example at approximately 60 to 80 degrees Celsius, for example approximately 70 degrees Celsius at for example a pressure of less than 15 millibar, for example less than 10 millibar. The concentrated product mixture may then be dissolved in more of the solvent S3 and transferred to a crystallisation vessel. The cooling in the crystallising C2 includes cooling to a temperature of approximately −20 to −40 degrees Celsius, for example −25 to −35 degrees Celsius, for example approximately −30 degrees Celsius, whilst taking into account acceptable accuracies of measurement. In examples, the method further includes seeding the crystallising C2 with a seeding amount of the compound represented by general formula (3). The seeding amount is an amount sufficient to initiate the crystallising C2 of the compound represented by general formula (3), the actual amount depending for example on the quantity of the product prepared. In some examples 0.1% wt or less in ratio with respect to the amount of the compound represented with general formula (2) may be added. Once the crystallising has occurred for a sufficiently long period of time to recover a desired amount of the product, the now solid and crystallised compound represented by general formula (3) may be collected by filtration. This may include washing the filtered product further, for example with an alcohol such as methanol and/or n-butanol. The product may then be dried and stored.

Figure 4:
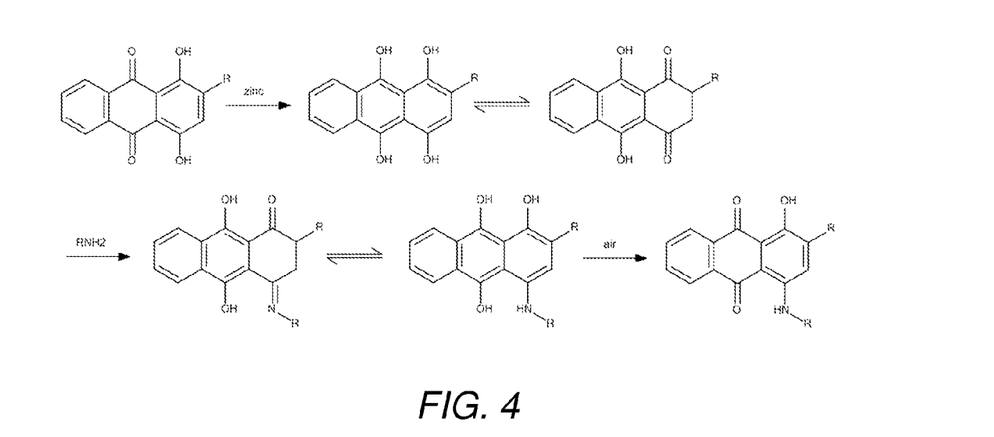
FIG. 4 shows schematically a non-limiting mechanism in relation to Reaction II described below.

In Reaction RII, it is believed without being limited to any theory that the compound represented by general formula (2) is reduced in situ by the reducing agent before the alkylamine then reacts with the reduced form of the compound represented by general formula (2). Referring, to FIG. 4, this is now illustrated schematically (noting that the label R is used for the purposes of illustration of alkyl groups generally, rather than R1 and R2, and noting again that it is to be appreciated that the mechanism shown is not to be taken as limiting, as this mechanism has not yet been confirmed):

A method of preparing the compound represented by general formula (3) may further include preparing the compound represented by general formula (2). For example, the method of preparing the compound represented by general formula (3) may include reacting a compound represented by general formula (1):

(1)

with an aldehyde represented by general formula (5):

(5)

to prepare the compound represented by general formula (2)

The compound represented by general formula (1) may otherwise be referred to as 2,3-dihydro-9,10-dihydroxy-1,4- anthracenedione, or Leucoquinizarin, and is available for example from Sigma Aldrich, 3050 Spruce St., St. Louis, Mo. 63103, USA.

The aldehyde represented by general formula (5) has a carbon atom having an oxygen linked to the carbon atom with a double bond, a hydrogen atom linked to the carbon atom with a single bond, and the alkyl group $R^1$ linked to the carbon atom by a single bond.

The reacting the compound represented by general formula (1) with the aldehyde may be represented schematically as follows:

Reaction RI:

The label "Reaction RI" will be used below to concisely refer to the reacting the compound represented by general formula (1) with the aldehyde.

In examples, either reaction RI or Reaction RII may be performed separately, or may be performed in the order Reaction RI then Reaction RII, to prepare the compound represented by general formula (3), with for example appropriate work up and crystallising after each or either of Reactions RI and RII.

In examples, Reaction RI is performed in the presence of an acid and a base. In some examples, Reaction RI is performed in the presence of a Brønsted-Lowry acid and a base, an acid and a Brønsted-Lowry base, or a Brønsted-Lowry acid and a Brønsted-Lowry base. A Brønsted-Lowry acid is typically a compound which can lose a proton thereby forming a conjugate base, and a Brønsted-Lowry base is typically a compound which can accept a proton to become a conjugate acid.

In examples, Reaction RI is performed in the presence of a carboxylic acid and an amine. A carboxylic acid group typically may be represented by the formula —COOH and is a group having a carbon atom linked to an —OH group by a single bond and an oxygen atom linked to the carbon atom by a double bond. A further group, for example an alkyl group, is linked to the carbon atom by a single bond as the skilled person will appreciate. The carboxylic acid may in examples be a monocarboxylic acid, in other words a group including one —COOH group, or a monocarboxylic acid containing 2 to 5 carbon atoms, i.e. 2, 3, 4 or 5 carbon atoms for example with one carbon being part of the —COOH group and at least one further of the carbon atoms being for example part of an alkyl group linked by a single bond to the carbon atom of the —COOH group.

An amine typically may be a primary, secondary or tertiary amine, in other words $NH_3$ with respectively one, two or three of the hydrogen atoms substituted by an alkyl group or an aryl group for example. In some examples the amine may be a cyclic amine, with the nitrogen atom forming part of the cyclic structure, or an aliphatic cyclic amine which is typically a cyclic amine without delocalisation within the cyclic structure, in other words a non-aromatic cyclic structure.

In some examples the Reaction RI is performed in the presence of ethanoic acid ($CH_3COOH$) and piperidine (($CH_2$)$_5NH$), which has been found to assist the Reaction RI to obtain a sufficient yield of the product.

In examples, the Reaction RI is performed in a solvent which in accordance with the earlier description is typically a liquid medium, vehicle or carrier, for example, in which a reaction can occur. This solvent is referred to below as S1 for clarity. In some examples, the solvent in which Reaction RI is performed includes an alcohol and in other examples is substantially an alcohol, for example solely an alcohol or an alcohol with tolerable impurities for example a trace amount of water. An alcohol is typically a compound, having for example an alkyl group with a hydroxyl group —OH linked with a single bond to a carbon atom of the alkyl group. The alkyl group may contain 2 to 5 carbon atoms and in some examples may be isopropanol, in other words 2-propanol ($CH_3CH$—$OHCH_3$), though in other examples may be a different alcohol.

In examples, Reaction RI is performed at a temperature in the range of for example approximately 70 to approximately 85 degrees Celsius, for example 70 to 85 degrees Celsius, or for example approximately 75 to 80 degrees Celsius, for example 75 to 80 degrees Celsius within acceptable accuracies for temperature measurements. After sufficient duration, for example when Reaction 1 is considered to have sufficiently run to completion, and for example when sufficient of the product of Reaction RI, namely the compound represented by general formula (2), has been produced, the reaction mixture may be cooled to approximately 40 to approximately 55 degrees Celsius, or to approximately 45 to approximately 50 degrees Celsius, or to 40 to 55 degrees Celsius, or 45 to 50 degrees Celsius within acceptable accuracies for temperature measurements.

In examples, after Reaction RI has occurred, the method includes crystallising the compound represented by general formula (2) from a solvent with cooling. This crystallising may be referred to herein as C1 and the solvent as S2. In some examples, no work up is required between Reaction RI and the crystallising C1, though in other examples a work up process may be used, for example depending on the solvent S2 used and whether that solvent S1 and the solvent S2 are the same.

In some examples, Reaction RI is performed in a solvent S1 which is the same solvent as the solvent S2 used in the crystallising C1. Therefore the solvent S2 may comprise, for example may substantially consist of, or solely consist of, within acceptable tolerances of impurities, any compound of the examples given above for solvent S1, for example isopropanol. It is to be noted that in some examples the compound of solvents S1 and S2 may be the same, but with more of that solvent compound being added to the reaction mixture after Reaction RI to provide the solvent S2. In other examples, the solvent S1 in the reaction mixture is sufficient in volume for the crystallising C1 to occur in the same volume of solvent in which Reaction RI occurred, without adding further solvent compound. Therefore, the volume of solvent S1 in Reaction RI may be the volume of solvent S2 in which the crystallising C1 is performed. With the solvents S1 and S2 being the same, phase A described below may be more efficiently conducted, without the extra expense of providing a different solvent than for Reaction RI for the crystallising C1, and also without the extra processing for example to remove the solvent from Reaction RI and then provide and then remove the solvent used in crystallising C1.

The method may for example further include seeding the crystallising C1 with a seeding amount of the compound represented by general formula (2). In some examples 0.05% wt or less with respect to the amount of the compound represented with general formula (1) may be added.

The cooling in the crystallising C1 includes cooling to a temperature of approximately −5 to approximately −20 degrees Celsius, for example approximately −10 to approximately −15 degrees Celsius, for example −5 to −20 or −10 to −15 degrees Celsius within acceptable accuracies for temperature measurement.

Once the crystallising C2 has occurred for a sufficiently long period of time to recover a desired amount of the product, the now solid and crystallised compound represented by general formula (2) may be collected by filtration. This may include washing the filtered product further, for example with an alcohol such as methanol. The product may then be dried and stored.

A specific example of a method of preparing the compound represented by general formula (3) will now be described. This example includes a specific example of Reaction RI, crystallising C1, Reaction RII, work up W1 and crystallising C2. It is to be appreciated that in further examples any one of Reaction RI, crystallising C1, Reaction RII, work up W1 and crystallising C2, for example any of the specific examples described below, may be combined with alternative examples of any one of Reaction RI, crystallising C1, Reaction RII, work up W1 and crystallising C2. As referred to in places below, Reaction RI and crystallising C1 may together be referred to as phase A, and Reaction RII, work up W1 and crystallising C2 may together be referred to as phase B.

Specific Example 1

Phase A

Reaction RI:
To a flask equipped with mechanical stirrer and nitrogen inlet was added 2-propanol (3.14 kg, 4.0 L), leucoquinizarin (2.0 kg, 8.25 mol), and 2-ethylhexanal (2.65 kg, 20.6 mol, 3.22 L). The reaction mixture was stirred for 15 minutes at room temperature until homogeneously mixed. In a separate flask a mixture was prepared by adding, respectively, 2-propanol (0.79 kg, 1.0 L), acetic acid (173 g, 165 mL), and piperidine (246 g, 285 mL). After stirring the mixture for 10 minutes, the latter mixture was added to the main reactor via a funnel. The funnel was rinsed with 2-propanol (0.39 kg, 0.5 L). The reaction mixture was warmed to 75-80° C. over two hours, in other words the increase in temperature to 75-80° C. took place during a two hour period (with "over" being used elsewhere herein with this meaning). The reaction mixture was heated at 75-80° C. for 16-20 hours. The conversion was monitored by measuring NMR indicating a conversion of 95%. The heater was removed and the reaction mixture was cooled to 45-50° C. over 1-2 hrs.
Crystallizing C1:
To initiate crystallization, seeding crystals of 2-(2-ethylhexyl)-1,4-dihydroxyanthracene-9,10-dione (1.0 gram) were added and the mixture was further stirred at room temperature for 2 hours. The reaction mixture was cooled to 10-15° C. and was stirred for 2-3 hours. The reaction mixture was filtered through an 8 L glass filter and the reactor was rinsed with methanol (1.59 kg, 2.0 L). The filter cake was washed with methanol (1.59 kg, 2.0 L) followed by drying the cake in a vacuum dryer for 16 hours at 50° C. The dried material was packed.
Yield: 2750 grams, 94.6% as an orange solid. Analysis: NMR conforms to structure, HPLC 98.7% purity.

Phase B

Reaction RII:
A nitrogen purged flask equipped with mechanical stirrer was charged with respectively, 2-(2-ethylhexyl)-1,4-dihydroxyanthracene-9,10-dione from Phase A (2.5 kg, 7.09 mol) and 2-ethylhexylamine (3.02 kg, 23.4 mol, 3.83 L). The reaction mixture was heated to 30° C. over one hour. To the reaction mixture was added zinc dust (162 g, 2.48 mol) and the mixture was heated to 40-45° C. over 30 minutes. To the reaction mixture water (250 g, 250 mL) was added drop-wise in 2-3 hours while maintaining the temperature between 45-55° C. The addition of water gives a slight exotherm. The reaction mixture was stirred at 50° C. for 30 minutes followed by heating the mixture to 60° C. over two hours. The reaction mixture was heated at 60° C. for three hours. The conversion was measured with NMR showing full conversion. The reaction mixture was cooled to room temperature overnight.
Work-Up W1:
In a separate flask a mixture was prepared of ice-water (5.0 kg, 5.0 L), acetic acid (2.10 kg, 2.0 L) and heptanes (5.13 kg, 7.5 L). The latter mixture was added to the reactor while stirring efficiently over 15 minutes. The glassware and funnel were rinsed with heptanes (1.71 kg, 2.5 L) and the heptanes were added to the reaction mixture. The stirring was stopped and the phases were allowed to separate. The aqueous phase (~9.0 L) was discarded. Methanol (1.58 L, 2.0 L) and water (150 g, 150 mL) were added respectively to the heptanes layer followed by stirring for 10 minutes. The layers were allowed to separate for 10 minutes, and the aqueous layer was discarded (~1.9 kg). The heptanes layer was washed with water (1.5 kg, 1.5 L) and stirred for 10 minutes. The phases were allowed to separate and the aqueous layer was discarded (1.5 kg). The organic hepanes phase was transferred to a rotary evaporator and the solution was concentrated at 60° C. at p<25 millibar (mbar).
Crystallising C2:
To the concentrate, n-butanol (1.21 kg, 1.5 L) was added and the volatiles were removed at 70° C. at p<10 mbar. A second amount of n-butanol (0.81 kg, 1.0 L) was added and the volatiles were removed at 70° C. at p<10 mbar. The concentrate was dissolved in n-butanol (8.10 kg, 10.0 L) and the mixture was transferred to a crystallization vessel. The glassware was rinsed with n-butanol (4.05 kg, 5.0 L) and the rinse was added to the crude product. The solution was stirred for 5 minutes followed by cooling to −30° C. over one hour. Seeding crystals of 2-(2-Ethylhexyl)-4-((2-ethylhexyl)amino)-1-hydroxyanthracene-9,10-dione (0.5 grams) were added and the mixture was stirred at −25° C. for three hours, followed by cooling to −35° C. over one hour. The solid material was filtered off on an 8 L glass filter. The filter cake was rinsed with a cooled (−20° C.) mixture of methanol (1.98 kg, 2.5 L) and n-butanol (2.0 kg, 2.5 L). The filter cake was washed three times with methanol (1.98 kg, 2.5 L). The product was transferred to a vacuum dryer and was dried at 30° C. for 16 hours. The product was collected and packed.

Yield: 2260 grams, 68.7% as a purple solid. Analysis: NMR conforms to structure, HPLC 97.3% purity.

As an example of an electrowetting application of the compound prepared to methods described above, FIG. 1 shows a diagrammatic cross-section of part of an example of an electrowetting display device 1, including a plurality of picture elements or display elements 2, one of which is shown in the Figure and which may also be referred to as an electrowetting pixel. Such a pixel or display element is an example of an electrowetting cell or an electrowetting element, the pixel or display element being an example of an electrowetting element for providing a display effect. The lateral extent of the display element is indicated in the Figure by two dashed lines 3, 4. The display elements comprise a first support plate 5 and a second support plate 6. The support plates may be separate parts of each display element, but the support plates may be shared in common by the plurality of display elements. The support plates may include a glass or polymer substrate 7a, 7b and may be rigid or flexible. The support plates in some examples include further layers and/or structures than illustrated, for example circuitry for controlling the display elements. Such features are not illustrated, for clarity.

Figures 1, 2:
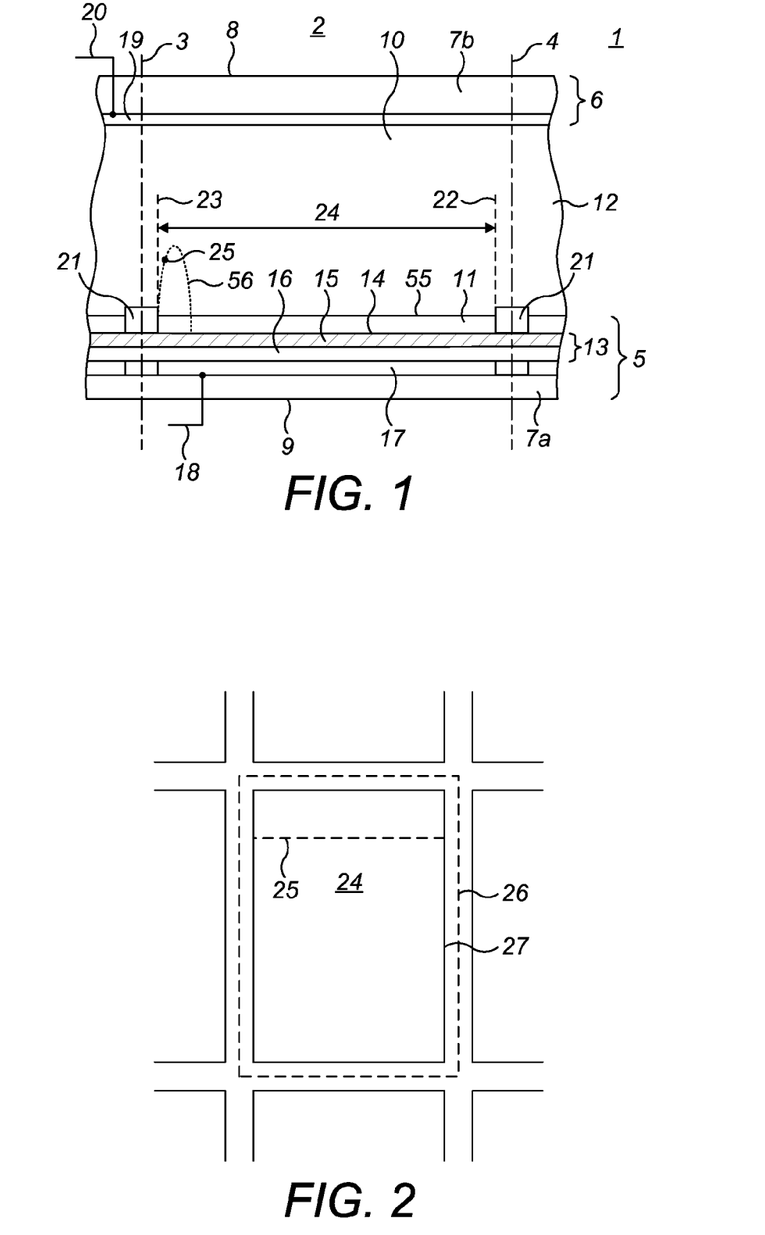
FIG. 1 shows schematically an example electrowetting display element.
FIG. 2 shows schematically a plan view of example display elements.

The display device has a viewing side 8 on which an image or display formed by the display device can be viewed and a rear side 9. In the Figure a surface of the first support plate 5, which surface is in this example a surface of the substrate 7a, is the rear side 9; a surface of the second support plate 6, which surface is in this example a surface of the substrate 7b, is the viewing side 8; alternatively, in other examples, a surface of the first support plate may be the viewing side. The display device may be of the reflective, transmissive or transflective type. The display device may be an active matrix driven or a direct drive display device as the skilled person will understand. The plurality of display elements may be monochrome. For a colour display device the display elements may be divided in groups, each group having a different colour; alternatively, an individual display element may be able to show different colours.

A space 10, which may otherwise be considered to be a chamber, of each display element between the support plates is filled with two fluids, for example liquids. In the example of FIG. 1, the space 10 is filled with a first layer of liquid 11 and a second layer of liquid 12. The liquid of the second layer is substantially immiscible with the liquid of the first layer. Therefore, the first layer and the second layer do not substantially mix with each other and in some examples do not mix with each other to any degree. With the first and second layers substantially not mixing with each other, it is envisaged in some examples that there may be some degree of mixing of the first and second layers, but that this is considered negligible in that the majority of the volume of first layer is not mixed with the majority of the volume of the second layer. The substantial immiscibility of the first and second layers is due to the properties of the first and second layers, for example their chemical compositions; the first and second layers tend to remain separated from each other, therefore tending not to mix together to form a homogeneous mixture. Due to this immiscibility, the liquids of the first and second layers meet each other at an interface labelled 55 in FIG. 1 for when no voltage is applied and labelled 56 for when a voltage is applied, which interface defines a boundary between the volume of the liquid of the first layer and the volume of the liquid of the second layer; this interface or boundary may be referred to as a meniscus. The location and shape of the interface between the first layer and the second layer in examples is determined by the applied voltage. The thickness of the first and second layers in FIG. 1 is shown as an example; in other examples, the first and/or second layers may have different thicknesses.

The liquid of the second layer of the device is at least one of electrically conductive or polar, i.e. the liquid of the second layer is electrically conductive, polar, or both, and may be water, or a salt solution such as a solution of potassium chloride in water. The liquid of the second layer may be transparent; it may instead be coloured, for example, or absorbing. The liquid of the first layer of the device, which is electrically non-conductive, may for example include an alkane like decane or hexadecane, silicone oil or decalin (otherwise known as bicyclo-4,4,0-decane).

The liquid of the first layer may absorb at least a part of the visible spectrum. The liquid of the first layer may be transmissive for a part of the visible spectrum, forming a colour filter. For this purpose the liquid of the first layer may be coloured by addition of pigment particles or a dye such as the compound represented by general formula (3) described above. Alternatively, the liquid of the first layer may be black, i.e. absorb substantially all parts of the visible spectrum, or reflecting. A reflective liquid may reflect the entire visible spectrum, making the layer appear white, or part of it, making it have a colour. In examples described herein, the liquid of the first layer is black and therefore absorbs substantially all parts of the optical spectrum, for example in the visible light spectrum. Typically, substantially absorbs for example includes a degree of variation, therefore the liquid of the first layer may not absorb all wavelengths, but the majority of wavelengths within a given spectrum such as the visible spectrum, so as to perform the function of the first layer in the element. The liquid of the first layer may therefore be configured to absorb substantially all light incident on the first layer. For example the liquid of the first layer may absorb 90% or more of light in the visible spectrum and incident on the first layer.

The support plate 5 includes a layer with a surface for adjoinment by a liquid such as the liquid of the first layer described herein. In examples described herein, the layer is an insulating layer 13. The insulating layer may be transparent, for example fully transparent, i.e. transmissive. The insulating layer 13 may extend between walls of a display element. To avoid short circuits between the second layer of liquid 12 and electrodes arranged under the insulating layer, layers of the insulating layer may extend uninterrupted over a plurality of display elements 2, as shown in the Figure. The insulating layer has a surface 14 facing, i.e. closest to, the space 10 of the display element 2. The thickness of the insulating layer may be less than 2 micrometers and may be less than 1 micrometer.

The insulating layer in examples described herein is for example formed of a layer 15 which is for example formed of a hydrophobic material such as Teflon AF1600® and a barrier layer 16 with predetermined dielectric properties, the layer 15 facing, i.e. being closer to, the space 10, as shown in the Figure. The barrier layer 16 may have a thickness, taken in a direction perpendicular to the plane of the substrate, between 50 nanometers and 500 nanometers and may be made of an inorganic material like silicon oxide or silicon nitride.

In the absence of an applied voltage, i.e. with the applied voltage being a zero voltage, the liquid of the first layer 11 adheres preferentially to the surface of the insulating layer 13 for adjoinment by the first layer, since the surface for adjoinment by the first layer has a higher, i.e. greater, wettability for the liquid of the first layer than for the liquid of the second layer; the surface may therefore be hydrophobic. As will be explained, with the applied voltage being a non-zero voltage, the surface has a higher wettability for the liquid of the second layer than for the liquid of the first layer; i.e. the surface with the applied non-zero voltage may be considered to be hydrophilic. Wettability relates to the relative affinity of a liquid for the surface of a solid. Wettability may be measured by the contact angle between a boundary of the liquid and the surface of the solid. The contact angle is determined by the difference in surface tension between the liquid and the solid at the liquid-solid boundary. For example, a high difference in surface tension can indicate hydrophobic properties. As the skilled person will appreciate, a material may be considered to be hydrophobic if the contact angle with water is greater than 90 degrees; a material may therefore be considered to be hydrophilic if the contact angle with water is less than 90 degrees.

Each display element 2 includes a first electrode 17 as part of the support plate 5. In examples shown there is one such electrode 17 per element; in other examples there may be more than one electrode per display element. The electrode 17 is electrically insulated from the first and second layers by the insulating layer 13; electrodes of neighbouring display elements are separated by a nonconducting layer. In some examples, further layers may be arranged between the insulating layer 13 and the electrode 17. The electrode 17 can be of any desired shape or form. The electrode 17 of a display element is supplied with voltage signals by a signal line 18, schematically indicated in the Figure.

The support plate 6 for example includes a second electrode 19, which may extend between walls of a display element, or be located above or covering the walls of the display element or extend uninterruptedly over a plurality of display elements 2, as shown in the Figure. The electrode 19 is in electrical contact with the liquid of the second layer 12 and is common to all display elements. The electrodes 17 and 19 may be made of for example the transparent conductive material indium tin oxide (ITO). A second signal line 20 is connected to the electrode 19. Alternatively, the electrode may be arranged at a border of the support plates, where it is in electrical contact with the liquid of the second layer. This electrode may be common to all elements, when they are liquidly interconnected by and share the liquid of the second layer, uninterrupted by walls. The display element 2 can be controlled by a voltage V applied between the signal lines 18 and 20. The signal line 18 can be coupled to a matrix of control lines on the substrate 7a. The signal line 18 and 20 are coupled to a display driving system.

The liquid of the first layer 11 in this example is confined to a display element by at least one wall, in this example walls 21, that follow the cross-section of the display element. The cross-section of a display element may have any shape; when the display elements are arranged in a matrix form, the cross-section is usually square or rectangular. Although the walls are shown as structures protruding from the insulating layer 13 and formed on a surface of the insulating layer 13, they may instead be a surface layer of the support plate that repels the liquid of the first layer, such as a hydrophilic or less hydrophobic layer. The walls may extend from the first to the second support plate but may instead extend partly from the first support plate to the second support plate as shown in FIG. 1.

The extent of the display element, indicated by the dashed lines 3 and 4, is defined by the center of the walls 21. The area of the surface between the walls of a display element, indicated by the dashed lines 22 and 23, is called the display area 24, over which a display effect occurs. The area of the surface on which the walls are formed may be referred to as the wall area. An extent of the surface 14 corresponding to the extent of the display area is in this example hydrophobic. The display effect depends on an extent that the liquids of the first and second layers adjoin the surface defined by the display area, in dependence on the magnitude of the applied voltage V described above. The magnitude of the applied voltage V therefore determines the configuration of the liquids of the first and second layers within the electrowetting element. In other words, the display effect depends on the configuration of the liquids of the first and second layers in the display element, which configuration depends on the magnitude of the voltage applied to the electrodes of the display element. The display effect gives rise to a display state of the display element for an observer looking at the display device. When switching the electrowetting element from one liquid configuration to a different liquid configuration the extent of the liquid of the second layer adjoining the display area surface may increase or decrease, with the extent of the liquid of the first layer adjoining the display area surface decreasing or increasing, respectively.

FIG. 2 shows a matrix of rectangular picture elements in a plan view of the hydrophobic surface of the first support plate. The extent of the central picture element in FIG. 2, corresponding to the dashed lines 3 and 4 in FIG. 1, is indicated by the dashed line 26. Line 27 indicates the inner border of a wall; the line 27 is also the edge of the display area 24.

When a zero or substantially zero voltage is applied between the electrodes 17 and 19, i.e. when the electrowetting element is in an off state, the liquid of the first layer 11 forms a layer between the walls 21, as shown in FIG. 1. Application of a voltage will retract the liquid of the first layer, for example against a wall as shown by the dashed shape 25 in FIG. 1 or FIG. 2. The controllable shape of the liquid of the first layer, in dependence on the magnitude of applied voltage, is used to operate the picture element as a light valve, providing a display effect over the display area 24. For example, switching the liquids of the first and second layers to increase adjoinment of the liquid of the second layer with the display area may increase the brightness of the display effect provided by the element. This display effect determines the display state an observer will see when looking towards the viewing side of the display device. The display state can be from black to white with any intermediate grey state; in a colour display device, the display state may also include colour.

The above examples are to be understood as illustrative. Further examples are envisaged. For example, although the compound represented by general formula (2) is described above in relation to Reactions RI and RII, it is to be understood that the compound represented by general formula (2) is considered new and hence is also described here, and is claimed in the accompanying claims, independently from the methods described previously.

It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the accompanying claims.

What is claimed is:

1. A method of preparing a compound corresponding to general formula (3):

(3)

wherein $R^1$ and $R^2$ are each independently an alkyl group, the method comprising:
reacting a compound corresponding to general formula (2):

(2)

with an alkylamine corresponding to general formula (4):

$$H_2N-R^2 \qquad (4).$$

2. A method according to claim 1, wherein the reacting the compound corresponding to general formula (2) with the alkylamine is performed in the presence of at least one of:
a reducing agent, or
water.

3. A method according to claim 2, wherein the reducing agent comprises at least one of:
zinc, or
magnesium.

4. A method according to claim 2, wherein a quantity of the reducing agent is less than a stoichiometric amount of the reducing agent.

5. A method according to claim 1, wherein $R^1$ is an alkyl group having 1 to 21 carbon atoms.

6. A method according to claim 1, wherein $R^2$ is an alkyl group having 1 to 22 carbon atoms.

7. A method according to claim 1, wherein $R^1$ is an alkyl group corresponding to general formula (6):

(6)

8. A method according to claim 1, wherein $R^2$ is an alkyl group corresponding to general formula (7):

(7)

9. A method according to claim 1, wherein the reacting a compound corresponding to general formula (2) with the alkylamine is performed without a solvent.

10. A method according to claim 1, wherein the reacting a compound corresponding to general formula (2) with the alkylamine is performed at a temperature in the range of approximately 25 to approximately 75 degrees Celsius.

11. A method according to claim 1, further comprising, after the reacting the compound corresponding to general formula (2) with the alkylamine:
crystallising the compound corresponding to general formula (3) from a solvent with cooling.

12. A method according to claim 11, wherein the solvent comprises an alcohol.

13. A method according to claim 11, wherein the cooling comprises cooling to a temperature of approximately −25 to approximately −35 degrees Celsius.

14. A method according to claim 1, wherein the method further comprises:
reacting a compound corresponding to general formula (1):

(1)

with an aldehyde corresponding to general formula (5):

$$H-CO-R^1 \qquad (5)$$

to prepare the compound corresponding to general formula (2).

15. A method according to claim 14, wherein the reacting the compound corresponding to general formula (1) with the aldehyde is performed in the presence of an acid and a base.

16. A method according to claim 14, wherein the reacting the compound corresponding to general formula (1) with the aldehyde is performed in the presence of: a carboxylic acid and an amine.

17. A method according to claim 14, wherein the reacting the compound corresponding to general formula (1) with the aldehyde is performed in the presence of ethanoic acid and piperidine.

18. A method according to claim 14, wherein the reacting the compound corresponding to general formula (1) with the aldehyde is performed in a solvent.

19. A method according to claim 18, wherein the solvent comprises an alcohol.

20. A method according to claim 14, further comprising:
crystallising the compound corresponding to general formula (2) from a solvent with cooling.

21. A method according to claim 20, wherein the cooling comprises cooling to a temperature of approximately −10 to approximately −15 degrees Celsius.

22. A method according to claim 14, wherein the reacting the compound corresponding to general formula (1) with the aldehyde to prepare the compound corresponding to general formula (2) is performed in a solvent, the method further comprising:
crystallising the compound corresponding to general formula (2) from the said solvent with cooling.

23. A method according to claim 22, wherein the solvent comprises isopropanol.

24. A method according to claim 11, wherein the solvent comprises n-butanol.

25. A method according to claim 18, wherein the solvent comprises isopropanol.

* * * * *